(12) United States Patent
Radhakrishna et al.

(10) Patent No.: US 9,128,079 B2
(45) Date of Patent: Sep. 8, 2015

(54) METHODS OF USING LUNG OR BRONCHIAL EPITHELIAL CELLS TO IDENTIFY BITTER TASTE MODULATORS

(75) Inventors: Harish Radhakrishna, Bridgewater, NJ (US); Michael D. Brown, Lilburn, GA (US); David Peter Siderovski, Chapel Hill, NC (US); Adam Kimple, Chapel Hill, NC (US); Staci Padove Cohen, Raleigh, NC (US)

(73) Assignees: The Coca-Cola Company, Atlanta, GA (US); The University of North Carolina, Chapel Hill, NC (US)

( * ) Notice: Subject to any disclaimer, the term of this patent is extended or adjusted under 35 U.S.C. 154(b) by 0 days.

(21) Appl. No.: 13/569,664

(22) Filed: Aug. 8, 2012

(65) Prior Publication Data

US 2013/0040316 A1 Feb. 14, 2013

Related U.S. Application Data

(60) Provisional application No. 61/521,129, filed on Aug. 8, 2011.

(51) Int. Cl.
*G01N 33/567* (2006.01)
*G01N 33/50* (2006.01)

(52) U.S. Cl.
CPC ........ *G01N 33/5044* (2013.01); *C12N 2503/02* (2013.01)

(58) Field of Classification Search
None
See application file for complete search history.

(56) References Cited

U.S. PATENT DOCUMENTS

| | | | |
|---|---|---|---|
| 4,115,538 A | 9/1978 | Satoh et al. |
| 4,132,770 A | 1/1979 | Barth |
| 4,146,501 A | 3/1979 | Henkin |
| 4,586,625 A | 5/1986 | Garrett |
| 4,677,126 A | 6/1987 | Janusz et al. |
| 4,692,512 A | 9/1987 | Janusz |
| 4,692,513 A | 9/1987 | Blum et al. |
| 4,883,888 A | 11/1989 | Gardlik |
| 4,896,303 A | 1/1990 | Leslie et al. |
| 4,918,103 A | 4/1990 | Park et al. |
| 4,940,056 A | 7/1990 | Heck et al. |
| 5,233,988 A | 8/1993 | Raghuprasad |
| 5,242,693 A | 9/1993 | Kurihara et al. |
| 5,275,823 A | 1/1994 | France et al. |
| 5,326,284 A | 7/1994 | Bohbot et al. |
| 5,447,869 A | 9/1995 | Okahata |
| 5,482,855 A | 1/1996 | Yamafuji et al. |
| 5,536,491 A | 7/1996 | Asai et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,637,618 A | 6/1997 | Kurtz et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,654,311 A | 8/1997 | Kurtz et al. |
| 5,665,755 A | 9/1997 | Kurtz et al. |
| 5,688,662 A | 11/1997 | Margolskee |
| 5,693,756 A | 12/1997 | Li et al. |
| 5,700,792 A | 12/1997 | Kurtz et al. |
| 5,703,053 A | 12/1997 | Kurtz et al. |
| 5,766,622 A | 6/1998 | Nelson |
| 5,785,984 A | 7/1998 | Kurihara et al. |
| 5,817,759 A | 10/1998 | Margoiskee |
| 5,866,608 A | 2/1999 | Kurtz et al. |
| 5,891,646 A | 4/1999 | Barak et al. |
| 5,910,508 A | 6/1999 | Thoreau et al. |
| 6,008,000 A | 12/1999 | Margolskee |
| 6,008,250 A | 12/1999 | Kurtz et al. |
| 6,015,792 A | 1/2000 | Kurtz et al. |
| 6,019,851 A | 2/2000 | Pittet et al. |
| 6,048,999 A | 4/2000 | Pajor et al. |
| 6,086,920 A | 7/2000 | Frisbee et al. |
| 6,110,693 A | 8/2000 | Barak et al. |
| 6,153,220 A | 11/2000 | Cumming et al. |
| 6,166,076 A | 12/2000 | Gilbertson |
| 6,242,029 B1 | 6/2001 | Pittet et al. |

(Continued)

FOREIGN PATENT DOCUMENTS

WO WO00/06593 2/2000

OTHER PUBLICATIONS

Robinett KS, et al. Am. J. Respir. Cell Mol. Biol. doi: 10.1165/rcmb.2011-0061OC. Epub Jun. 3, 2011.*
Doggrell SA, Expert Opin Ther Targets. Jul. 2011;15(7):899-902. doi: 10.1517/14728222.2011.580279. Epub Apr. 27, 2011.*
Tizzano M, et al. BMC Pulmonary Medicine 2011, 11:3 doi:10.1186/1471-2466-11-3.*
Despande DA et al., Nat Med. Nov. 2010;16(11):1299-1304. doi: 10.1038/nm.2237. Epub Oct. 24, 2010.*
Dehkordi O, et al. Life Sci. Feb. 13, 2010;86(7-8):281-8. doi: 10.1016/j.lfs.2009.12.016. Epub Jan. 10, 2010.*

(Continued)

*Primary Examiner* — Robert Landsman
(74) *Attorney, Agent, or Firm* — King & Spalding

(57) ABSTRACT

Provided herein are cell lines and assays that can be utilized to identify taste receptor modulators.

23 Claims, 8 Drawing Sheets

(56) References Cited

U.S. PATENT DOCUMENTS

| | | |
|---|---|---|
| 6,245,376 B1 | 6/2001 | Pittet et al. |
| 6,251,193 B1 | 6/2001 | Rossy et al. |
| 6,251,463 B1 | 6/2001 | Rossy et al. |
| 6,270,807 B1 | 8/2001 | Danielson et al. |
| 6,273,719 B1 | 8/2001 | Whitman |
| 6,306,372 B1 | 10/2001 | Stier et al. |
| 6,352,851 B1 | 3/2002 | Nielsen et al. |
| 6,383,778 B1 | 5/2002 | Zuker et al. |
| 6,420,527 B1 | 7/2002 | Bolen et al. |
| 6,461,658 B1 | 10/2002 | Merkel et al. |
| 6,475,510 B1 | 11/2002 | Venkatesh et al. |
| 6,540,978 B1 | 4/2003 | Margolskee et al. |
| 6,558,910 B2 | 5/2003 | Zuker et al. |
| 6,608,176 B2 | 8/2003 | Chaudhari et al. |
| 6,623,939 B1 | 9/2003 | Zuker et al. |
| 6,815,176 B1 | 11/2004 | Zuker et al. |
| 6,818,747 B2 | 11/2004 | Yao et al. |
| 6,875,574 B1 | 4/2005 | Zuker |
| 6,893,827 B1 | 5/2005 | Palmer et al. |
| 6,913,906 B2 | 7/2005 | Bolen et al. |
| 6,929,925 B1 | 8/2005 | Zuker et al. |
| 6,942,874 B2 | 9/2005 | McGregor et al. |
| 6,955,887 B2 | 10/2005 | Adler et al. |
| 6,998,144 B2 | 2/2006 | Merkel et al. |
| 7,000,718 B2 | 2/2006 | Adachi et al. |
| 7,018,812 B2 | 3/2006 | Oakley et al. |
| 7,022,488 B2 | 4/2006 | Servant et al. |
| 7,030,630 B2 | 4/2006 | Haas et al. |
| 7,041,457 B2 | 5/2006 | Yao et al. |
| 7,052,857 B2 | 5/2006 | Zoller et al. |
| 7,087,394 B2 | 8/2006 | Johnson et al. |
| 7,105,650 B2 | 9/2006 | Adler |
| 7,122,365 B2 | 10/2006 | Nielsen et al. |
| 7,125,564 B2 | 10/2006 | Chen et al. |
| 7,144,733 B2 | 12/2006 | Miesenbock et al. |
| 7,179,614 B2 | 2/2007 | Margolskee et al. |
| 7,186,819 B2 | 3/2007 | San Gabriel et al. |
| 7,196,190 B2 | 3/2007 | Ning et al. |
| 7,208,290 B2 | 4/2007 | Li et al. |
| 7,223,551 B2 | 5/2007 | Adler et al. |
| 7,227,302 B2 | 6/2007 | Iida et al. |
| 7,241,880 B2 | 7/2007 | Adler et al. |
| 7,244,584 B2 | 7/2007 | Zuker et al. |
| 7,244,835 B2 | 7/2007 | Adler et al. |
| 7,270,967 B2 | 9/2007 | Zuker et al. |
| 7,279,338 B2 | 10/2007 | Kim et al. |
| 7,282,557 B2 | 10/2007 | Zuker et al. |
| 7,287,557 B2 | 10/2007 | Bunke et al. |
| 7,291,485 B2 | 11/2007 | Yao et al. |
| 7,294,474 B2 | 11/2007 | Zoller et al. |
| 7,297,543 B2 | 11/2007 | Zoller et al. |
| 7,297,772 B2 | 11/2007 | Zoller et al. |
| 7,301,009 B2 | 11/2007 | Zoller et al. |
| 7,303,886 B2 | 12/2007 | Zoller et al. |
| 7,309,577 B2 | 12/2007 | Zoller et al. |
| 7,314,716 B2 | 1/2008 | Huang et al. |
| 7,314,725 B2 | 1/2008 | Drayna et al. |
| 7,332,292 B2 | 2/2008 | Oakley et al. |
| 7,335,479 B2 | 2/2008 | Zuker |
| 7,335,487 B2 | 2/2008 | Liao et al. |
| 7,338,771 B2 | 3/2008 | Pronin et al. |
| 7,341,842 B2 | 3/2008 | Margolskee et al. |
| 7,344,845 B2 | 3/2008 | Han et al. |
| 7,344,859 B2 | 3/2008 | Zoller et al. |
| 7,344,882 B2 | 3/2008 | Lee et al. |
| 7,354,753 B2 | 4/2008 | Nielsen et al. |
| 7,364,867 B2 | 4/2008 | Margolskee et al. |
| 7,364,903 B2 | 4/2008 | Zoller et al. |
| 7,368,285 B2 | 5/2008 | Zoller et al. |
| 7,371,546 B2 | 5/2008 | Svendsen |
| 7,374,878 B2 | 5/2008 | Stryer et al. |
| 7,393,654 B2 | 7/2008 | Adler |
| 7,396,651 B2 | 7/2008 | Adler |
| 7,396,663 B2 | 7/2008 | Burford et al. |
| 7,399,601 B2 | 7/2008 | Adler |
| 7,402,400 B2 | 7/2008 | Zuker et al. |
| 7,402,415 B2 | 7/2008 | Nair et al. |
| 7,405,283 B2 | 7/2008 | Sampson et al. |
| 7,407,765 B2 | 8/2008 | Li et al. |
| 7,407,769 B2 | 8/2008 | Zuker et al. |
| 7,413,867 B2 | 8/2008 | Bufe et al. |
| 7,419,791 B2 | 9/2008 | Adler et al. |
| 7,435,552 B2 | 10/2008 | Adler et al. |
| 7,452,685 B2 | 11/2008 | Adler et al. |
| 7,452,694 B2 | 11/2008 | Zuker et al. |
| RE40,594 E | 12/2008 | Margolskee et al. |
| 7,459,277 B2 | 12/2008 | Erienbach et al. |
| 7,459,532 B2 | 12/2008 | Lee et al. |
| 7,465,550 B2 | 12/2008 | Zuker et al. |
| 7,476,399 B2 | 1/2009 | Tachdjian et al. |
| 7,479,373 B2 | 1/2009 | Zuker et al. |
| 7,488,599 B2 | 2/2009 | Rawson et al. |
| 7,504,481 B2 | 3/2009 | Lee et al. |
| 7,507,544 B2 | 3/2009 | Adler et al. |
| 7,507,793 B2 | 3/2009 | Zuker et al. |
| 7,517,972 B2 | 4/2009 | Adler et al. |
| 7,524,637 B2 | 4/2009 | Adler et al. |
| 7,527,944 B2 | 5/2009 | Li et al. |
| 7,534,577 B2 | 5/2009 | Adler et al. |
| 7,541,158 B2 | 6/2009 | Li et al. |
| 7,542,162 B2 | 6/2009 | Muratani |
| 7,579,453 B2 | 8/2009 | Drayna et al. |
| 7,588,900 B2 | 9/2009 | Zuker et al. |
| 7,588,916 B2 | 9/2009 | Adler et al. |
| 7,595,166 B2 | 9/2009 | Zuker et al. |
| 7,598,430 B2 | 10/2009 | Weeks et al. |
| 7,601,513 B2 | 10/2009 | Zoller et al. |
| 7,601,883 B2 | 10/2009 | Zuker et al. |
| 7,611,848 B2 | 11/2009 | Gaven et al. |
| 7,622,258 B2 | 11/2009 | Sampson et al. |
| 7,629,134 B2 | 12/2009 | Matsunami et al. |
| 7,638,289 B2 | 12/2009 | Adler |
| 7,655,422 B2 | 2/2010 | Adler et al. |
| 7,704,698 B2 | 4/2010 | Adler |
| 7,705,121 B2 | 4/2010 | Adler et al. |
| 7,718,383 B2 | 5/2010 | Adler |
| 7,723,051 B2 | 5/2010 | Adler |
| 7,723,481 B2 | 5/2010 | Adler |
| 7,736,862 B2 | 6/2010 | Adler |
| 7,737,254 B2 | 6/2010 | Adler et al. |
| 7,745,601 B2 | 6/2010 | Zuker et al. |
| 7,763,431 B1 | 7/2010 | Zoller et al. |
| 7,772,385 B2 | 8/2010 | Adler et al. |
| 7,776,561 B2 | 8/2010 | Pronin et al. |
| 2002/0119526 A1 | 8/2002 | Zuker et al. |
| 2002/0160424 A1 | 10/2002 | Adler et al. |
| 2002/0164645 A1 | 11/2002 | Zuker et al. |
| 2003/0008344 A1 | 1/2003 | Adler et al. |
| 2003/0022288 A1 | 1/2003 | Zuker et al. |
| 2003/0036630 A1 | 2/2003 | Zuker et al. |
| 2003/0040045 A1 | 2/2003 | Zuker et al. |
| 2003/0054448 A1 | 3/2003 | Adler et al. |
| 2003/0101001 A1 | 5/2003 | Huang |
| 2003/0148448 A1 | 8/2003 | Liao et al. |
| 2003/0166137 A1 | 9/2003 | Zuker et al. |
| 2003/0220479 A1 | 11/2003 | Li et al. |
| 2003/0232407 A1 | 12/2003 | Zoller et al. |
| 2004/0108149 A1 | 6/2004 | Adachi et al. |
| 2004/0132075 A1 | 7/2004 | Elliot et al. |
| 2004/0171042 A1 | 9/2004 | Adler et al. |
| 2004/0175792 A1 | 9/2004 | Zoller et al. |
| 2004/0175793 A1 | 9/2004 | Zoller et al. |
| 2004/0185469 A1 | 9/2004 | Zoller et al. |
| 2004/0191805 A1 | 9/2004 | Adler et al. |
| 2004/0191862 A1 | 9/2004 | Zoller et al. |
| 2004/0209286 A1 | 10/2004 | Adler et al. |
| 2004/0214239 A1 | 10/2004 | Servant et al. |
| 2004/0219632 A1 | 11/2004 | Margolskee et al. |
| 2004/0229239 A1 | 11/2004 | Adler et al. |
| 2005/0032158 A1 | 2/2005 | Adler et al. |
| 2005/0048508 A1 | 3/2005 | Ariyasu et al. |
| 2005/0084506 A1 | 4/2005 | Tachdjian et al. |
| 2005/0084932 A1 | 4/2005 | Zoller et al. |
| 2005/0085625 A1 | 4/2005 | Li et al. |

(56) References Cited

U.S. PATENT DOCUMENTS

| | | |
|---|---|---|
| 2005/0106571 A1 | 5/2005 | Erlenbach et al. |
| 2005/0164310 A1 | 7/2005 | Zuker et al. |
| 2005/0177886 A1 | 8/2005 | Margolskee et al. |
| 2005/0181461 A1 | 8/2005 | Zuker |
| 2005/0244810 A1 | 11/2005 | Egan et al. |
| 2005/0260599 A1 | 11/2005 | Ryba et al. |
| 2005/0287517 A1 | 12/2005 | Adler et al. |
| 2006/0014208 A1 | 1/2006 | Zoller et al. |
| 2006/0040255 A1 | 2/2006 | Ookura et al. |
| 2006/0045953 A1 | 3/2006 | Tachdjian et al. |
| 2006/0127977 A1 | 6/2006 | Zoller et al. |
| 2006/0134693 A1 | 6/2006 | Servant et al. |
| 2006/0160176 A1 | 7/2006 | Zoller et al. |
| 2006/0257543 A1 | 11/2006 | Tachdjian et al. |
| 2006/0275765 A1 | 12/2006 | Slack et al. |
| 2007/0003680 A1 | 1/2007 | Tachdjian et al. |
| 2007/0037134 A1 | 2/2007 | Servant et al. |
| 2007/0042435 A1 | 2/2007 | Zuker et al. |
| 2007/0054266 A1 | 3/2007 | Sato et al. |
| 2007/0065884 A1 | 3/2007 | Zuker et al. |
| 2007/0104709 A1 | 5/2007 | Li et al. |
| 2007/0105159 A1 | 5/2007 | Erlenbach et al. |
| 2007/0161053 A1 | 7/2007 | Li et al. |
| 2007/0166728 A1 | 7/2007 | Abramson |
| 2007/0185312 A1 | 8/2007 | Zuker et al. |
| 2008/0039534 A1 | 2/2008 | Radhakrishna et al. |
| 2008/0187936 A1 | 8/2008 | Li et al. |
| 2009/0311686 A1 | 12/2009 | Slack et al. |
| 2013/0131108 A1* | 5/2013 | Liggett et al. ............... 514/313 |

OTHER PUBLICATIONS

Deshpande DA, et al. Nature Medicine, 16(11):1299-1305, Nov. 2010.*

Cohen SP, et al. J. Biol. Chem. 287(50):41706-41719, Dec. 7, 2012.*

White SR, et al. Am. J. Physiol. 259(4 Pt 1):L294-L303, Oct. 1990.*

Aaronson et al., Human Sarcoma Cells in Culture, Experimental Cell Research, 61:1-5 (1970).

Akabas et al., A Bitter Substance Induces a Rise in Intracellular Calcium in a Subpopulation of Rat Taste Cells, Science, 242:1047-1050 (1988).

Bachmanov et al., Taste Receptor Genes, Annu. Rev. Nutr., 27:389-414 (2007).

Behrens et al., Gustatory Expression Pattern of the Human TAS2R Bitter Receptor Gene Family Reveals a Heterogenous Population of Bitter Responsive Taste Receptor Cells, J. Neuroscience, 27(46):12630-12640 (2007).

Bohn et al., Seeking Ligand Bias: Assessing GPCR Coupling to Beta-Arrestins for Drug Discovery, Drug Discov. Today Technol., 7(1):e37-e42 (2010).

Chandrashekar et al., The Receptors and Cells for Mammalian Taste, Nature, 444:288-294 (2006).

Cooper et al., [$^{35}$S]GTP$_\gamma$S binding G protein-coupled receptor assays, Methods Mol. Biol., 552:143-151 (2009).

Danilova et al., Comparison of the Responses of the Chorda Tympani and glossopharyngeal nerves to taste stimuli in C57BL/6J Mice, BMC Neuroscience, 4:5 (Mar. 2003).

Danilova et al., Sense of Taste in a New World Monkey, the Common Marmoset: Recordings from the Chorda Tympani and Glossopharyngeal Nerves, J. Neurophysiol., 88:579-594 (2002).

Danilova et al., Responses of Single Taste Fibers and Whole Chorda Tympani and Glossopharyngeal Nerve in the Domestic Pig, Chem. Senses, 24:301-316 (1999).

Danilova et al., Gustatory Responses of the Hamster *Mesocricetus auratus* to Various Compounds Considered Sweet by Humans, J. Neurophysiol., 80:2102-2112 (1998).

De Los Frailes et al., Screening technologies for G protein-coupled receptors: from HTS to uHTS, Methods Mol. Biol., 552:15-37 (2009).

Di Certo et al., Delayed internalization and lack of recycling in a beta2-adrenergic receptor fused to the G protein alpha-subunit, BMC Cell Biol., 9:56 (2008).

Farbman et al., Evidence for a Novel Mechanism of Binding and Release of Stimuli in the Primate Taste Bud, J. Neuroscience, 9(10):3522-3528 (1989).

Felley-Bosco et al., Constitutive expression of inducible nitric oxide synthase in human bronchial epithelial cells induces c-fos and stimulates the cGMP pathway, Am. J. Resp. Cell and Mol. Biol., 11:159-164 (1994).

Fujiyama et al., Intracellular free calcium concentration in human taste bud cells increases in response to taste stimuli, FEBS Letters, 434:47-50 (1998).

Harding et al., Direct analysis of a GPCR-agonist interaction by surface plasmon resonance, Eur. Biophys. J., 35(8):709-712 (2006).

Hellekant et al., Primate Sense of Taste: Behavioral and Single Chorda Tympani and Glossopharyngeal Nerve Fiber Recordings in the Rhesus Monkey, *Macaca mulatta*, J. Neurophysiol., 77:978-993 (1997).

Kershaw et al., Analysis of Chemokine Receptor Endocytosis and Intracellular Trafficking, Methods Enzymol., 460:357-377(2009).

Liu et al., A multiplex calcium assay for identification of GPCR agonists and antagonists, Assay Drug Dev. Technol., 8(3):367-379 (2010).

Liu et al., Comparison on functional assays for Gq-coupled GPCRs by measuring inositol monophospate-1 and intracellular calcium in 1536-well plate format, Curr. Chem. Genomics, 1:70-78 (2008).

Offermanns et al., $G\alpha_{15}$ and $G\alpha_{16}$ Couple with a Wide Variety of Receptors to Phospholipase C, J. Bio. Chem., 270:15175-15180 (1995).

Ogura et al., Bitter Taste Transduction of Denatonium in the Mudpuppy *Necturus maculosus*, J. Neuroscience, 17(10):3580-3587 (1997).

Orola et al., Intracellular Free Calcium Concentration in Single Taste Receptor Cells in the Guinea Pig, Acta Otolaryngol (Stockh),112:120-127 (1992).

Salamon et al., Chapter 6. Plasmon Resonance Methods in Membrane Protein Biology Applications to GPCR Signaling, Methods Enzymol., 461:123-146 (2009).

Shah et al., Motile Cilia of Human Airway Epithelia are Chemosensory, Science, 325(5944):1131-1134 (2009).

Strachan et al., Ribosomal S6 kinase 2 directly phosphorylates the 5-hydroxytryptamine 2A (5-HT$_{2A}$) serotonin receptor, thereby modulating 5-HT$_{2A}$ signaling, J. Biol. Chem., 284:5557-5573 (2009).

Williams et al., GPCR signaling: understanding the pathway to successful drug discovery, Methods Mol. Biol., 552:39-50 (2009).

\* cited by examiner wt = wildtype RGS21; R>E = point-mutated loss-of-fcn RGS21

16-HBE:

METHODS OF USING LUNG OR BRONCHIAL EPITHELIAL CELLS TO IDENTIFY BITTER TASTE MODULATORS

CROSS REFERENCE TO RELATED APPLICATIONS

This application claims benefit of and priority to U.S. Provisional Application No. 61/521,129 filed Aug. 8, 2011, the contents of which are hereby incorporated by reference in their entirety.

REFERENCE TO SEQUENCE LISTING

The Sequence Listing submitted Aug. 8, 2012, as a text file named "10031014US1_ST25.txt," created on Aug. 7, 2012, and having a size of 13.6 kilobytes is hereby incorporated by reference.

BACKGROUND

Numerous tastants are utilized in consumables. Additionally, agents can modulate bitter taste, for example by decreasing bitter taste in consumables, such as foods, beverages and medicines. Means for screening agents to identify tastants and to identify modulators of bitter receptors are thus useful.

SUMMARY

This disclosure relates to cell lines and assays that can be utilized to identify taste receptor modulators. For example, provided herein is a method for identifying a bitter taste modulator comprising contacting a cell with a bitter tastant and a test compound, wherein the cell is derived from airway tissue and endogenously expresses bitter taste receptor, and measuring bitter taste receptor activity. Optionally, the cell can endogenously express RGS21. A change in bitter taste receptor activity by the bitter tastant in the presence of the test compound indicates modulation of the bitter taste receptor by the test compound, thus identifying a bitter taste modulator.

Further provided is a method for identifying a bitter tastant comprising, contacting a cell, wherein the cell is derived from airway tissue and endogenously expresses a bitter taste receptor, with a test compound and measuring bitter taste receptor activity. Optionally, the cell can endogenously express RGS21. An increase in bitter taste receptor activity indicates that the test compound is a bitter tastant.

Further provided is an isolated, relatively pure population of airway cells that express a bitter taste receptor. The receptor is optionally endogenously expressed by the airway cell, but the airway cell can be genetically modified to express one or more bitter taste receptors or to overexpress one or more bitter taste receptors. Optionally, the cell can endogenously express RGS21 but can also be genetically modified to express RGS21 or to overexpress RGS21.

Also provided is a method for identifying a bitter tastant or modulator comprising contacting a cell with a test compound and measuring taste receptor activity, wherein the cell is a 16HBE cell or a derivative thereof that is derived from airway tissue and endogenously expresses a taste receptor.

DETAILED DESCRIPTION

Figure 1:
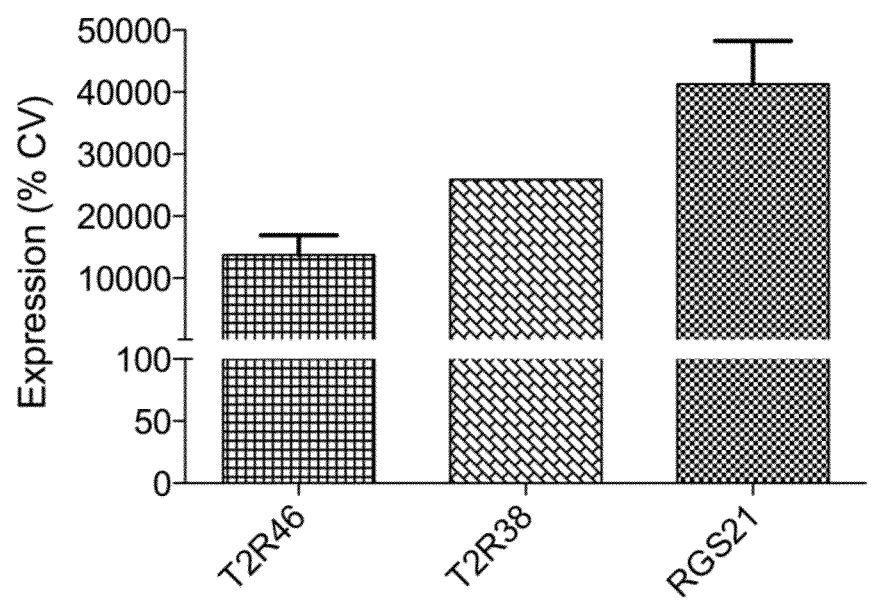
FIG. 1 shows that 16HBE cells express T2R38, T2R46 and RGS21 as determined by RT-PCR.

Uses for Cell Lines Comprising Bitter Taste Receptors

Provided herein is a method for identifying a bitter taste modulator comprising contacting a cell with a bitter tastant and a test compound, wherein the cell is derived from airway tissue and endogenously expresses a bitter taste receptor, and measuring bitter taste receptor activity. Optionally, the cell can endogenously express RGS21. A change in bitter taste receptor activity by the bitter tastant in the presence of the test compound indicates modulation of the bitter taste receptor by the test compound, thus identifying a bitter taste modulator.

As used throughout, a bitter taste modulator is a compound that modulates bitter taste receptor activity, for example, by inhibiting or blocking bitter taste receptor activation by a bitter tastant, or by enhancing bitter taste receptor activation by a bitter tastant. In one example, the methods of identifying bitter taste modulators identify compounds that modulate, preferably block or inhibit, the activation of a bitter taste receptor by a bitter tastant. As used throughout, such blockers or inhibitors act directly on the receptor but can optionally act upstream or downstream of the receptor.

Any cell derived from airway tissue that endogenously expresses a bitter taste receptor can be utilized in the methods set forth herein. For example, lung or bronchial cells, such as lung or bronchial epithelial cells can be utilized. Known human airway cell lines can optionally be utilized. Examples of airway cells that can be utilized include, but are not limited to, 16HBE cells and cells derived from 16HBE cells wherein the cells express a bitter taste receptor.

In the methods set forth herein, the bitter taste receptor responds to at least one bitter tastant or bitterant. Bitter tastants include, but are not limited to, acesulfame K, acetaminophen, 2-acetyl pyrazine, aloin, amino-2-norbornane-carboxylic acid, amygadalin, andrographolide, arbutin, aristolochic acid, atropine, brucine, 4-benzylpiperidine, caffeine, chloramphenicol, chloroquine, cinchonine, ciprofloxacin, clarithromycin, clindamycin, cycloheximide, cyclooctanone, denatonium benzoate, dexamethasone, diltiazem hydrochloride, diisobutylamine, dimethylbiguanide, 2,6-dimethylpiperidine, doxepin, enalapril maleate, edrophonium, enoxacin, (–)-epicatechin, (–)-erythromycin, ethylpyrazine, famotidine, gabapentin, ginkgolide A, goitrin, guaicol glyceryl ether, labetalol-HCl, linamarin, lomefloxacin, (–)-lupinine, N-methylthiourea, 1-methy-2-quinolinone, methylprednisolone, nitrophthalene, nitrosaccharin, ofloxacin, oleuropein, omeprazole, oxybutynin chloride, oxyphenonium HBr, peptide-LPFNQL (SEQ ID NO:1), peptide-LPFSQL (SEQ ID NO: 2), peptide-YQEPVLGPVRGPFPIIV (SEQ ID NO: 3), peptide-PVLGPVRGPFPIIV (SEQ ID NO: 4), peptide-PVRGPFPIIV (SEQ ID NO: 5), peptide-RGPFPIIV (SEQ ID NO: 6), N-ethyl-N'-phenylurea, 2-picoline, picric acid, pirenzepine dihydrochloride, phenylthiocarbamide, prednisone, procainamide, 6-n-propyl-2-thiouracil, quassin, quinacrine, quinine, ranitidine, saccharin, D-(–)-salicin, spartein sulfate pentahydrate, sucrose octaacetate, strychnine, sulfamethoxazole, theobromine, thioacetanilide, thiocarbanilide, tolazoline, tolylurea, trapidil, trimethoprim, and L-tryptophan.

As used throughout, a test compound can be a naturally occurring compound, a protein, a peptide, a polysaccharide, a chemical, a small molecule or a polynucleotide (for example, a cDNA, an aptamer, a morpholino, a triple helix molecule, an siRNA, a shRNA, an miRNA, an antisense RNA, an LNA, a ribozyme or any other polynucleotide now known or identified in the future). In the methods set forth herein, the compound can be in a library. The libraries can comprise natural products or synthetic compounds. Therefore, provided herein are methods for screening libraries of compounds in order to identify a bitter taste modulator or a bitter tastant. RGS21 is also known as a regulator of G-protein signaling 21 and is capable of binding to or inhibiting Gαi class proteins or other Gα proteins. As set forth above, the airway cells utilized in the present methods can optionally endogenously express RGS21. RGS21 can be encoded by a nucleotide sequence comprising the human sequence set forth in GenBank Accession No. AY643711.1 (SEQ ID NO: 7) This nucleotide sequence encodes the protein sequence set forth in GenBank Accession No. NP_001034241.1 (SEQ ID NO: 8). Airway cells from human or other species comprising an RGS21 nucleotide sequence or an RGS21 protein sequence that is at least 60%, 65%, 70%, 75%, 80%, 85%, 90%, 95%, 95%, 97%, 98%, 99% or more identical to the sequence set forth in GenBank Accession No. AY643711.1 or the sequence set forth in GenBank Accession No. NP_001034241.1, respectively, can also be utilized in the methods described herein. Optionally, the protein sequence comprises one or more conservative amino acid substitutions as compared to the provided sequence. In particular, cells comprising an RGS21 sequence, wherein the RGS21 retains at least one activity of RGS21, for example, interaction with a Gα protein can be utilized in the methods set forth herein.

The cells described herein can be genetically modified to express or overexpress RGS21. For example, an airway cell described herein can be genetically modified by introducing an exogenous nucleic acid comprising a nucleotide sequence encoding RGS21. The nucleic acid can be stably or transiently introduced into the cell. A cell that is genetically modified includes a cell wherein the introduced nucleic acid is also endogenous to the cell. The exogenous nucleic acid can be in a construct or vector that comprises a promoter that is operably linked to the nucleotide sequence encoding RGS21. The promoter can be a constitutive promoter or an inducible promoter. Exemplary inducible promoters include tissue-specific promoters and promoters responsive or unresponsive to a particular stimulus (such as light, oxygen or chemical concentration, for example, a tetracycline inducible promoter).

As utilized throughout, Gα proteins include all members of the $G\alpha_i$ class now known or later discovered, including but not limited to, $G\alpha_{i1}$, $G\alpha_{i2}$, and $G\alpha_{i3}$, gustducin, transducin, $G\alpha_o$, $G\alpha_{tr}$, $G\alpha_g$, $G\alpha_{tr}$, $G\alpha_{tc}$ and $G\alpha_z$. Also included are all members of the Gq class now known or later discovered, including but not limited to, $G\alpha_q$ $G\alpha_{11}$ $G\alpha_{14}$, $G\alpha_{15}$ and $G\alpha_{16}$. The cells described herein can comprise one or more types of Gαi that are endogenously or recombinantly expressed in the cells. The cells can also comprise chimeric Gα proteins, for example $G\alpha_q$-Gustducin or $G\alpha_{16}$-gustducin 44 as described in U.S. Patent Publication No. 20090311686, incorporated in its entirety by this reference.

The bitter taste receptor can be selected from any bitter taste receptor, including, for example, T2R46 or T2R38. T2R46 is also known as taste receptor type 2, member 46 of the G protein-coupled receptor family and mediates the perception of bitterness through a G protein-coupled second messenger pathway. An example of a nucleotide sequence encoding T2R46 is the human sequence set forth in GenBank Accession No. NM_176887.2 (SEQ ID NO: 9). This sequence encodes the protein sequence set forth in GenBank Accession No. NP_795368.2 (SEQ ID NO: 10). Airway cells from human or other species endogenously comprising a T2R46 nucleotide sequence or a T2R46 protein sequence that is at least 60%, 65%, 70%, 75%, 80%, 85%, 90%, 95%, 95%, 97%, 98%, 99% or more identical to the sequence set forth in GenBank Accession No. NM_176887.2, or GenBank Accession No. NP_795368.2, can be utilized in the methods set forth herein. Optionally, the protein sequence comprises one or more conservative amino acid substitutions as compared to the provided sequence. In particular, cells comprising a T2R46 sequence, wherein the T2R46 receptor retains the ability to respond to at least one bitter tastant, can be used in the methods described herein.

T2R38 is also known as taste receptor type 2, member 38 of the G protein-coupled receptor family and also mediates the perception of bitterness through a G protein-coupled second messenger pathway. An example of a nucleotide sequence encoding T2R38 is the human sequence set forth in GenBank Accession No. NM_176817.4 (SEQ ID NO: 11). This sequence encodes the protein sequences set forth in GenBank Accession No. NP_789787.4 (SEQ ID NO: 12). Airway cells from human or other species endogenously comprising a T2R38 nucleotide sequence or a T2R38 protein sequence that is at least 60%, 65%, 70%, 75%, 80%, 85%, 90%, 95%, 95%, 97%, 98%, 99% or more identical to the sequence set forth in GenBank Accession No. NM_176817.4 or GenBank Accession No. NP_789787.4, can be utilized in the methods set forth herein. Optionally, the protein sequence comprises one or more conservative amino acid substitutions as compared to the provided sequence. In particular, cells comprising a T2R38 sequence, wherein the T2R38 receptor retains the ability to respond to at least one bitter tastant, can be used in the methods described herein.

The cells described herein can be genetically modified to express or overexpress the bitter taste receptor. For example, an airway cell described herein can be genetically modified by introducing an exogenous nucleic acid comprising a nucleotide sequence encoding T2R46 or T2R38. The nucleic acid can be stably or transiently introduced into the cell. A cell that is genetically modified includes a cell wherein the introduced nucleic acid is also endogenous to the cell. The exogenous nucleic acid can be in a construct or vector that comprises a promoter that is operably linked to the nucleotide sequence encoding T2R46 or T2R38. The promoter can be a constitutive promoter or an inducible promoter. Exemplary inducible promoters include tissue-specific promoters and promoters responsive or unresponsive to a particular stimulus (such as light, oxygen or chemical concentration, for example, a tetracycline inducible promoter).

In the methods described herein, the cell(s) can be grown on an appropriate substrate, such as a multi-well plate, a tissue culture dish, a flask, etc. The cell can be in a population of cells. This population can be an isolated, relatively pure population of airway cells. One of skill in the art would know how to select the appropriate growth conditions and medium for a given cell type. The methods described herein can further comprise contacting the cell with a dye, substrate, assay medium or any other composition necessary to assess the output from a signaling pathway. For example, the method can comprise loading the cells with calcium-sensitive fluorescent dye in order to measure changes in cytoplasmic calcium levels. The incubation periods necessary to effect bitter taste activation and subsequent assessment of bitter taste receptor activity will vary by cell type but can be empirically determined by one of skill in the art. The cell(s) can be contacted with a test compound before, during or after contacting the cells with the bitter tastant. Screening methods can optionally be performed in vivo. Therefore, the cell can be in a subject.

In the methods described throughout, taste receptor activity can be measured by any means standard in the art. Any suitable physiological change that is a consequence of G protein-coupled receptor activity can be used to assess the effect of a test compound on a taste receptor. Methods for assaying G protein coupled receptor activity are available in the art (see Williams and Hill "GPCR signaling: understanding the pathway to successful drug discovery," *Methods Mol Biol.* 2009; 552:39-50 (2009); and De los Frailes and Diez "Screening technologies for G protein-coupled receptors: from HTS to uHTS," *Methods Mol Biol.* 552:15-37 (2009)).

One of skill in the art can measure changes in the level of a second messenger in the cell. Examples of second messengers include, cAMP, cGMP, diacylglycerol (DAG), Phosphatidylinositol 4,5-bisphosphate (PIP2), inositol 1,4,5-trisphosphate (IP$_3$) and intracellular calcium. For example, changes in intracellular cAMP or cGMP can be measured using immunoassays. The method described in Offermanns & Simon, *J. Bio. Chem.*, 270:15175-15180 (1995), can be used to determine the level of cAMP. Also, the method described in Felley-Bosco et al., *Am. J. Resp. Cell and Mol. Biol.*, 11:159-164 (1994), can be used to determine the level of cGMP. Further, an assay kit for measuring cAMP and/or cGMP is described in U.S. Pat. No. 4,115,538, incorporated herein by this reference.

Activation of some G protein-coupled receptors stimulates the formation of inositol triphosphate (IP$_3$) through phospholipase C-mediated hydrolysis of phosphatidylinositol. IP$_3$ stimulates the release of intracellular calcium ions. Thus, a change in cytoplasmic calcium ion levels, or a change in second messenger levels such as IP$_3$ can be used to assess G protein-coupled receptor function. Increased cytoplasmic calcium levels can result from the release of intracellular calcium stores as well as from extracellular calcium entry via plasma membrane ion channels. Methods for measuring changes in cytoplasmic calcium levels are available to those of skill in the art. For example, calcium levels can be measured fluorescent $Ca^{2+}$ indicator dyes and fluorimetric imaging (See Liu et al. "A multiplex calcium assay for identification of GPCR agonists and antagonists," *Assay Drug Dev Technol.* June; 8(3):367-79 (2010); and Liu et al. "Comparison on functional assays for Gq-coupled GPCRs by measuring inositol monophospate-1 and intracellular calcium in 1536-well plate format," *Curr Chem Genomics.* 2008 Jul. 11; 1:70-8 (2008)).

RGS21 GTPase activating protein (GAP) activity can also be measured to assess receptor activity. For example, one of skill in the art can measure a change in the interaction between RGS21 and a G protein, for example, a Gα protein. This interaction can be measured by fluorescence resonance energy transfer, immunoassay or any other means for measuring the interaction between two proteins. Also, radiolabelled (or fluorescent) GTPγS binding to isolated membrane preps from cells expressing the appropriate endogenous tastant receptor can be measured (See, for example, Cooper et al. "[35S]GTPgammaS binding G protein-coupled receptor assays" Methods Mol. Biol. 552:143-151 (2009)). In these methods, activation of the receptor leads to guanine nucleotide exchange on the heterotrimeric G-protein, leading the G-alpha subunit to bind (irreversibly) to the radiolabeled (or fluorescent) GTPγS.

Binding activity can also be used to measure taste receptor activity, for example, via competitive binding assay or surface plasmon resonance (see Salamon et al. "Chapter 6. Plasmon resonance methods in membrane protein biology applications to GPCR signaling," *Methods Enzymol.* 2009; 461:123-46 (2009); and Harding et al. "Direct analysis of a GPCR-agonist interaction by surface plasmon resonance," *Eur Biophys J. October;* 35(8):709-12 (2006).

Receptor internalization and/or receptor desensitization can also be measured (see, for example, Kershaw et al. "Analysis of chemokine receptor endocytosis and intracellular trafficking," *Methods Enzymol.* 460:357-77(2009); and Di Certo et al. "Delayed internalization and lack of recycling in a beta2-adrenergic receptor fused to the G protein alpha-subunit," *BMC Cell Biol.* October 7; 9:56(2008)). Receptor-dependent activation of gene transcription can also be measured to assess taste receptor activity. The amount of transcription may be measured by using any method known to those of skill in the art. For example, mRNA expression of the protein of interest may be detected using PCR techniques, microarray or Northern blot. The amount of a polypeptide produced by an mRNA can be determined by methods standard in the art for quantitating proteins in a cell, such as Western blotting, ELISA, ELISPOT, immunoprecipitation, immunofluorescence (e.g., FACS), immunohistochemistry, immunocytochemistry, etc., as well as any other method now known or later developed for quantitating protein in or produced by a cell.

Beta-arrestin recruitment and/or receptor desensitization is optionally measured. See, for example, Bohn et al., "Seeking Ligand Bias: Assessing GPCR Coupling to Beta-Arrestins for Drug Discovery. *Drug Discov Today Technol.* Spring; 7(1): e37-e42 (2010).

Taste receptor dependent physical changes to a cell can also be measured, for example, by microscopically assessing size, shape, density or any other physical change mediated by taste receptor activation. Flow cytometry can also be utilized to assess physical changes and/or determine the presence or absence of cellular markers.

This method can further comprise contacting the cell with a second bitter tastant, after contacting the cell with the test compound and the first bitter tastant and prior to measuring bitter taste receptor activity. The first bitter tastant and the second bitter tastant can be the same or different.

When measuring a change in bitter taste receptor activity, bitter receptor activity in a cell contacted with a test compound and a bitter tastant can be compared to bitter receptor activity in a control cell contacted with a bitter tastant, but not contacted with the test compound. Bitter taste receptor activity can also be compared to bitter taste receptor activity in the same cell prior to addition of the test compound or after the effect of the test compound has subsided. For example, decreased concentration of cAMP can occur upon bitter receptor activation. If an increase in cAMP concentration is measured in a cell contacted with a test compound and a bitter tastant as compared to a cell contacted with the bitter tastant, the test compound is a bitter taste modulator that inhibits activation of a bitter taste receptor by the bitter tastant. If a decrease in cAMP concentration is measured in a cell contacted with a test compound and a bitter tastant as compared to a cell contacted with the bitter tastant, the test compound is a bitter taste modulator that enhances activation of a bitter taste receptor by the bitter tastant. In another example, increased release of intracellular calcium can occur upon bitter receptor activation. If a decrease in intracellular calcium is measured in a cell contacted with a test compound and a bitter tastant as compared to a cell contacted with the bitter tastant, the test compound is a bitter taste modulator that inhibits activation of a bitter taste receptor by the bitter tastant. If an increase in intracellular concentration is measured in a cell contacted with a test compound and a bitter tastant as compared to a cell contacted with the bitter tastant, the test compound is a bitter taste modulator that enhances activation of a bitter taste receptor by the bitter tastant. These examples are merely exemplary as any parameter described herein can be measured and compared to appropriate control cells to measure changes in bitter taste receptor activity affected by test compounds.

This method can further comprise measuring the effect of the identified bitter taste modulator in a human or other taste tests in order to evaluate the effect of the bitter taste modulator on bitter taste. Any of the bitter taste modulators identified via the methods described herein can be used in foods, beverages and medicines as flavor or taste modulators in order to inhibit the bitter taste associated with beverages, foods or medicines.

As utilized throughout, consumables include all food products, including but not limited to, cereal products, rice products, tapioca products, sago products, baker's products, biscuit products, pastry products, bread products, confectionery products, dessert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof.

This method can further comprise comparing bitter receptor activity in a cell contacted with an identified bitter taste modulator and a known bitter tastant with bitter receptor activity in a control cell contacted with a known bitter taste modulator and a known bitter tastant. One of skill in the art would know that known bitter taste modulators have established potencies or activity levels. By comparing bitter taste modulators identified by the methods described herein with known bitter taste modulators, potencies can be established for the identified bitter taste modulators. Depending on the amount of bitter taste receptor activity necessary for a particular food, beverage, medicine or process, one of skill in the art can select one or more of the bitter taste modulators identified by the methods set forth herein based on its potency. The bitter taste modulators identified by the methods set forth herein can be combined with known bitter tastants, sweeteners, umami tastants, bitter taste modulators, sweet taste modulators, umami taste modulators or any combination thereof.

Further provided is a method for identifying a bitter tastant comprising contacting a cell, wherein the cell is derived from airway tissue and endogenously expresses a bitter taste receptor with a test compound, and measuring bitter taste receptor activity. Optionally, the cell endogenously expresses RGS21. An increase in bitter taste receptor activity indicates that the test compound is a bitter tastant.

When measuring bitter taste receptor activity, bitter receptor activity in a cell contacted with a test compound can be compared to bitter receptor activity in a control cell not contacted with the test compound. Bitter taste receptor activity can also be compared to bitter taste receptor activity in the same cell prior to addition of the test compound or after the effect of the test compound has subsided. For example, decreased concentration of cAMP can occur upon bitter receptor activation. If a decrease in cAMP concentration is measured in a cell contacted with a test compound as compared to a control cell not contacted with the test compound, the test compound is a bitter tastant. In another example, increased release of intracellular calcium can occur upon bitter receptor activation. If an increase in intracellular calcium concentration is measured in a cell contacted with a test compound as compared to a control cell not contacted with the test compound, the test compound is a bitter tastant. These examples are merely exemplary as any parameter described herein can be measured and compared to appropriate control cells to measure bitter taste receptor activity effected by test compounds.

This method can further comprise measuring the effect of the identified bitter tastant in a human or other taste tests in order to evaluate the effect of the bitter tastant on bitter taste. Any of the bitter tastants identified via the methods described herein can be used in consumables such as foods, beverages and medicines in order to increase bitterness associated with beverages, foods or medicines. Alternatively, any of the bitter tastants identified via the methods described herein can be selectively removed from beverages, foods or medicines or the processes utilized to make beverages, food and medicines in order to reduce bitterness.

This method can further comprise comparing bitter receptor activity in a cell contacted with an identified bitter tastant with bitter receptor activity in a control cell contacted with a known bitter tastant. One of skill in the art would know that known bitter tastants have established potencies or activity levels. By comparing bitter tastants identified by the methods described herein with known bitter tastants, potencies can be established for the identified bitter tastants. Depending on the amount of bitter taste receptor activity necessary for a particular food, beverage, medicine or process, one of skill in the art can select one or more of the bitter tastants identified by the methods set forth herein based on its potency. The bitter tastants identified by the methods set forth herein can be combined with known bitter tastants, sweeteners or umami tastants.

Cell Lines

Further provided is an isolated, relatively pure population of airway cells that express a bitter taste receptor. The bitter taste receptor can be T2R46 or T2R38. Optionally, the cells endogenously express the bitter taste receptor and RGS21 but endogenously expressing cells can be modified to overexpress bitter taste receptors.

Also provided is a population of cells that can be utilized to assess bitter taste receptor activity for a test compound. For example, a population of airway cells that endogenously express a bitter taste receptor can be contacted with the test compound. Taste receptor activity can be measured in the cells as described herein. The test compound can then be identified as a bitter tastant. Optionally, at the initial screening stage, a combined population of airway cells in which a subset expresses one receptor and another subset expresses a different receptor could be used. If this combined population provides a positive effect, subsequent tests can be performed with cell populations expressing only one type of receptor for more specific analysis.

Similarly, a population of airway cells that endogenously express a bitter taste receptor can be contacted with a bitter tastant and the test compound. Taste receptor activity can be measured in the cells as described herein. The test compound can be then be identified as a bitter taste modulator.

For example, a population of 16HBE cells can be utilized to assess bitter taste receptor activity. These examples are not meant to be limiting as the cell can be any airway cell that endogenously expresses a bitter taste receptor. The cell can optionally express RGS21.

As used herein, the terms isolated and relatively pure refer to a state of purification greater than that which occurs naturally. In particular, isolated populations of cells described herein are substantially free from the materials with which the cells are normally associated in nature. By relatively pure is meant in a percentage of purity that exceeds nature, including for example 80% to 100% pure or any value in between.

As used in the specification and the appended claims, the singular forms "a, an and the" include plural referents unless the context clearly dictates otherwise. The term or refers to a single element of stated alternative elements or a combination of two or more elements, unless the context clearly indicates otherwise. As used herein, comprises means includes. Thus, comprising A or B, means "including A, B, or A and B, without excluding additional elements.

The following examples are put forth so as to provide those of ordinary skill in the art with a complete disclosure and description of how the compounds and/or methods claimed herein are made and evaluated, and are intended to be purely exemplary of the invention and are not intended to limit the scope of what the inventors regard as their invention except as and to the extent that they are included in the accompanying claims. Efforts have been made to ensure accuracy with respect to numbers (e.g., amounts, temperature, etc.), but some errors and deviations should be accounted for.

EXAMPLES

Cell lines were selected that endogenously express a bitter taste receptor. These cells lines include, but are not limited to, 16HBE. 16HBE cells express RGS21 as well as bitter taste receptors T2R46 and T2R38 (FIG. 1).

Functional Assay Using Tastants

Transient Gene Overexpression

16-HBE cells were seeded onto 6 well plates at a density of $3 \times 10^5$ cells per well and incubated in DMEM supplemented with 10% fetal bovine serum (FBS), 4 mM L-glutamine, 100 U/ml penicillin, and 100 µg/ml streptomycin at 37° C. in a 5% $CO_2$/95% air atmosphere. After 24 hours, media was replaced with fresh media. Plasmid DNA (1.5 µg) and FuGENE 6 (Roche; Indianapolis, Ind.) were complexed and added dropwise to each well, per the manufacturer's instructions. Cell monolayers were incubated an additional 24 hours prior to use in the FLIPR assay for transient intracellular calcium mobilization.

Stable Gene Underexpression

Stable 16-HBE cell lines were generated via lentiviral infection. pLK0.1 plasmids encoding human RGS21-directed shRNA (Oligo IDs TRCN0000036859, TRCN0000036861, and TRCN0000036863; generated by The RNAi Consortium and purchased from Open Biosystems as catalog # RH53979-9604267, RH53979-98492449, and RH53979-9604271) were prepared from bacterial stocks via maxiprep (Qiagen; Valencia, Calif.) and packaged into a lentiviral vector by the UNC Lineberger Comprehensive Cancer Center Lenti-shRNA Core Facility. A control empty lentiviral vector (Open Biosystems; Huntsville, Ala. (catalog #RHS4080)) was also packaged to establish the negative control cell line. These viruses were used to infect separate 16-HBE cell cultures seeded onto 100 mm dishes at 50% confluency. Stably-transfected cell lines were selected with puromycin (Cellgro; Manassas, Va.) and maintained in standard media supplemented with puromycin for several weeks prior to use in the FLIPR assay.

GloSensor cAMP Assays

Twenty-four hours post-transfection, cells were re-plated on poly-D-lysine-treated, clear-bottom, white 384-well plates at a density of 15,000 cells/well. Forty-eight hours post-transfection, culture medium was aspirated and cells were washed once with assay medium (DMEM (without FBS or phenol), 15 mM HEPES pH 7.4) before being incubated for 2 hours with 20 ill/well of equilibration medium (assay medium with 4% GloSensor™ substrate (Promega; Madison, Wis.)). After two hours, 10 µl of 3× final concentration denatonium benzoate (diluted in 3 µM forskolin-containing assay medium) was added to each well and allowed to incubate for 10 minutes before GloSensor™ emission was read on a MicroBeta Plate Counter (PerkinElmer; Waltham, Mass.). Before plotting, luminescence counts were normalized to 100% maximal response for each condition to account for variability in GloSensor™ expression, transfection efficiency, and the exact number of cells per well.

Fluorescence Imaging Plate Reader (FLIPR) calcium Flux Assays

Calcium flux assays were performed as previously described in Strachan et al., "Ribosomal S6 kinase 2 directly phosphorylates the 5-hydroxytryptamine 2A (5-HT2A) serotonin receptor, thereby modulating 5-HT2A signaling," *J Biol Chem* 284:5557-5573 (2009). 16-HBE cells were trypsinized, counted, and seeded onto clear-bottomed 96 well plates (Greiner Bio-One; Monroe, N.C.) pre-coated with poly-D-lysine, at a density of $7.5 \times 10^5$ cells per well. After a 24 hour incubation, media was removed and replaced with a $Ca^{2+}$ assay buffer (20 mM HEPES, 1x HBSS, 2.5 mM probenecid, and $Ca^{2+}$ assay dye, pH 7.4) (FLIPR® Calcium Assay Kit; Molecular Device Corp, Sunnyvale, Calif.). After a 1-hour incubation at 37° C., during which the cells were allowed to take up the dye, fluorescence responses of cells were measured with a FLIPRTETRA (Molecular Device Corp; Sunnyvale, Calif.) device upon the addition of variable concentrations of tastant, or vehicle, in the presence of assay buffer (20 mM HEPES, pH 7.4, 1× Hanks Balanced Salt [Invitrogen; Carlsbad, Calif.] and 2.5 mM probenecid). After data acquisition, a subsequent addition of 5 mM thapsigargin was injected into each well, and fluorescence was measured again. Net peak responses to tastants were normalized to net peak responses to thapsigargin. Responses were compared with that of wild-type control 16-HBE cells. Statistical and graphical analyses were performed using Prism v. 5.0b (GraphPad Software; La Jolla, Calif.).

Results

16HBE cells were selected for bitter taste stimulation. The cells were loaded with fluorescent calcium-sensitive dye, treated with a variety of tastants, and monitored for intracellular calcium release with a FLIPR imaging device.

Figure 2:
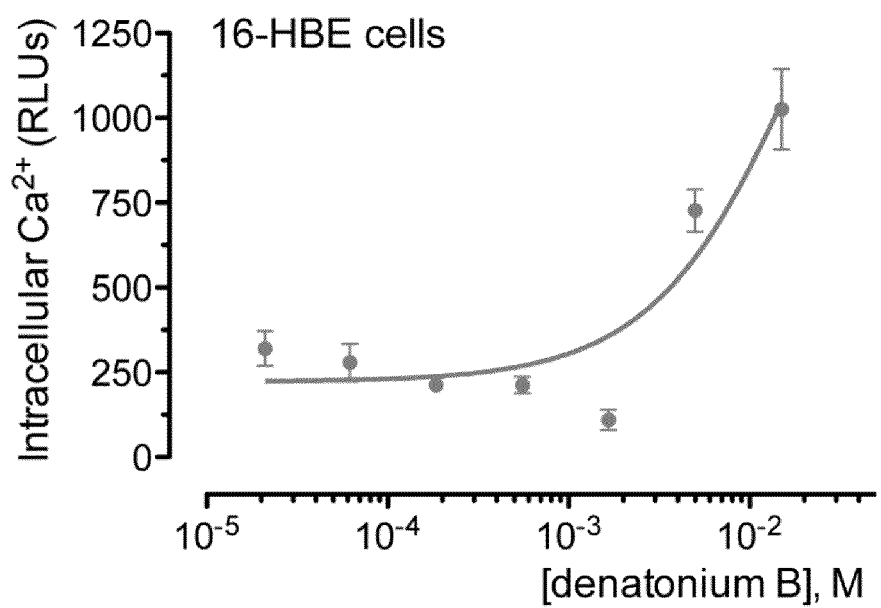
FIG. 2 shows that 16HBE cells respond to increasing concentrations of the bitter compound, denatonium-B, as demonstrated by an increase in intracellular calcium.
Figure 3:
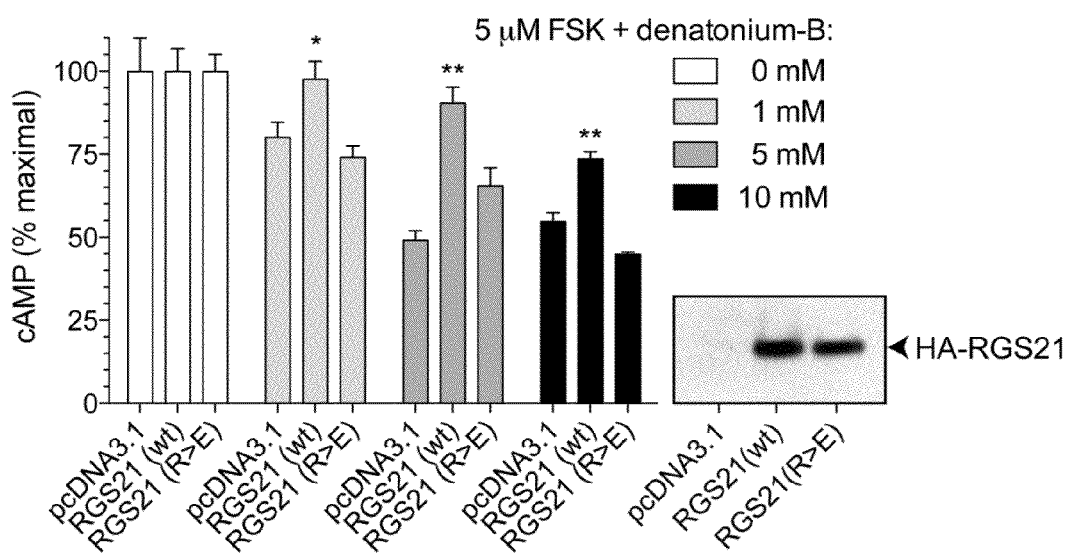
FIG. 3 shows that 16HBE cells respond to increasing concentrations of denatonium-B, by decreasing the concentration of intracellular cyclic AMP, as expected upon activation of a bitter receptor. Also shown is that overexpression of the wildtype form of RGS21 blunts bitter signaling and increases cAMP levels. Inhibition of forskolin-stimulated cAMP production by treatment with indicated concentrations of denatonium-B was determined 24 hours post-transfection by detection of Promega's cAMP GloSensor-dependent luminescence.
Figure 4:
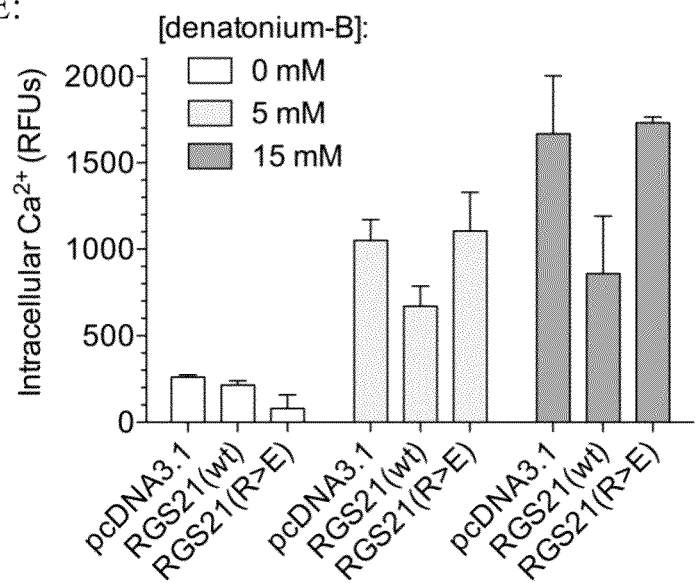
FIG. 4 shows that overexpression of the wildtype form of RGS21, reduces the denatonium-induced calcium response in 16HBE cells.
Figure 5:
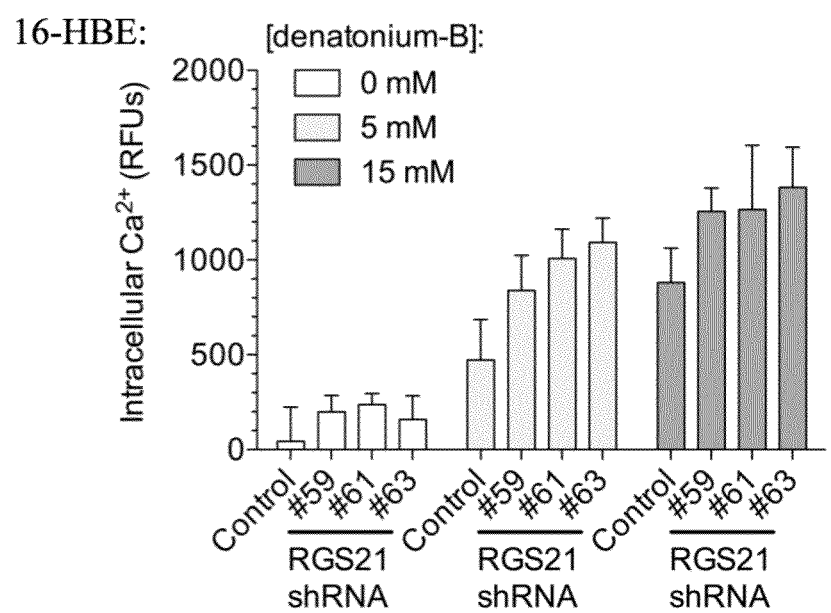
FIG. 5 shows that knocking down cellular expression of RGS21 in 16HBE cells with shRNA increases the magnitude of the denatonium-induced calcium response.
Figure 6:
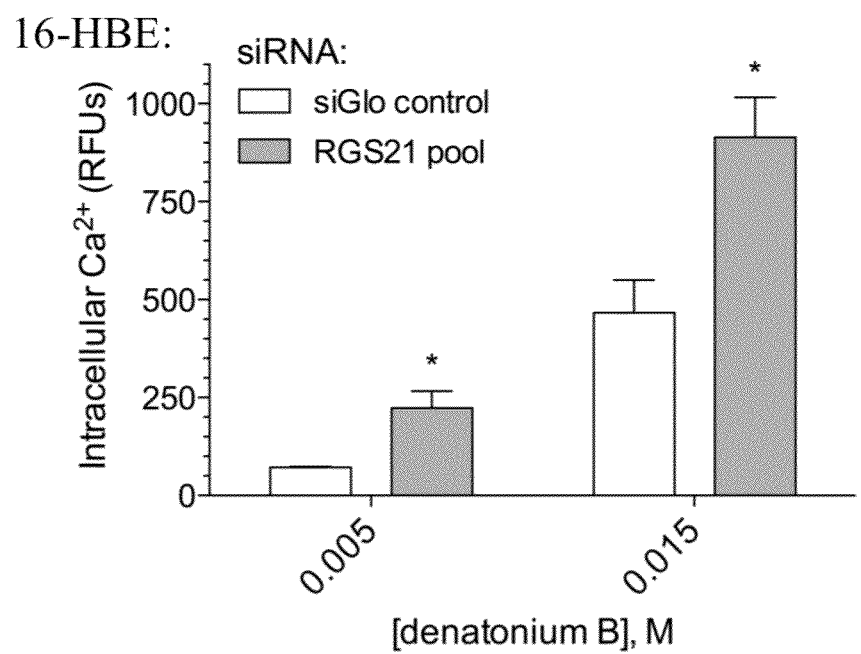
FIG. 6 shows that knocking down cellular expression of RGS21 in 16HBE cells with siRNA increases the magnitude of the denatonium-induced calcium response.
Figure 7:
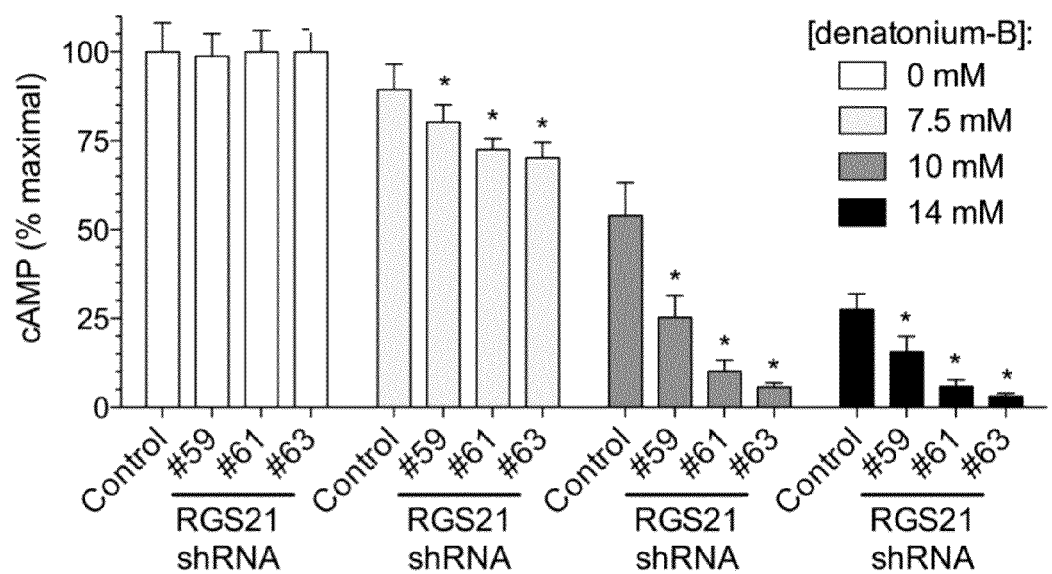
FIG. 7 shows that knocking down cellular expression of RGS21 in 16HBE cells enhances bitter signaling and decreases cAMP levels.
Figure 8:
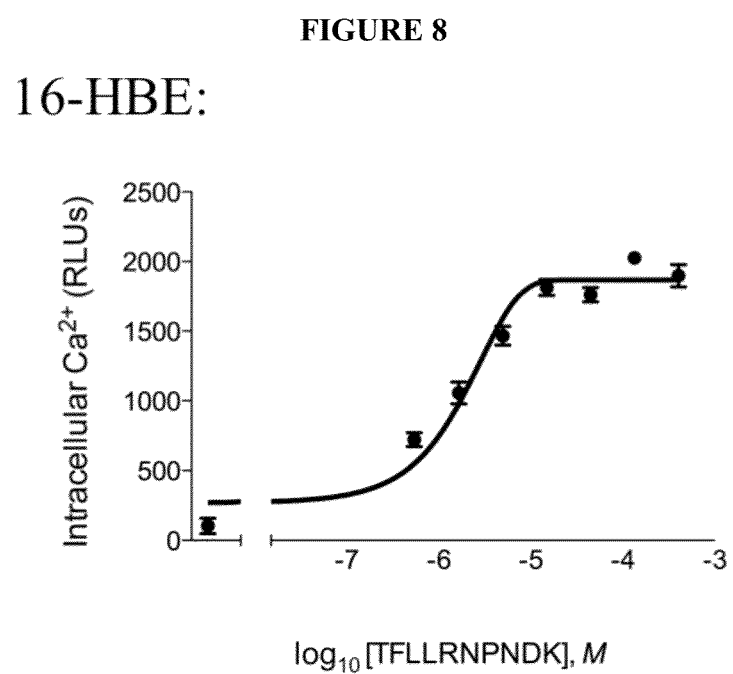
FIG. 8 shows that 16-HBE cells respond to increasing concentrations of the protease-activated receptor PAR-1 agonist peptide, a non-tastant GPCR agonist.

As shown in FIG. 2, 16HBE cells respond to increasing concentrations of the bitter compound, denatonium-B, as demonstrated by an increase in intracellular calcium, an expected consequence of activation of bitter receptors. Overexpression of the wildtype form of RGS21, reduces the denatonium-induced calcium response in 16HBE cells (FIG. 3). Conversely, knocking down cellular expression of RGS21 in 16HBE cells increases the magnitude of the denatonium-induced calcium response (FIGS. 5 and 6). 16HBE cells respond to increasing concentrations of denatonium-B, by decreasing the concentration of intracellular cyclic AMP, as expected upon activation of a bitter receptor (FIG. 3). Knocking down cellular expression of RGS21 in 16HBE cells enhances bitter signaling and decreases cAMP levels (FIG. 7). Also shown is that 16-HBE cells respond to increasing concentrations of the protease-activated receptor PAR-1 agonist peptide, a non-tastant GPCR agonist (FIG. 8).

These results show that 16HBE cells can be used for the cell-based detection of bitterants, or bitter tastants.

What is claimed is:

1. A method for identifying a candidate bitter taste modulator for potency testing comprising:
   a) contacting a cell with a bitter tastant and a test compound, wherein the cell is a lung or bronchial epithelial cell derived from airway tissue and endogenously expresses a bitter taste receptor;
   b) measuring bitter taste receptor activity, wherein a change in bitter taste receptor activity by the bitter tastant indicates modulation of the bitter taste receptor by the test compound, thus identifying a bitter taste modulator, and
   c) identifying a candidate bitter taste modulator for potency testing.

2. The method of claim 1, wherein the cell endogenously expresses Regulator of G-protein signaling-21 (RGS21).

3. The method of claim 1, wherein the modulator inhibits the activity of the bitter tastant on the bitter taste receptor.

4. The method of claim 1, wherein the bitter taste receptor is Taste receptor type 2, member 46 (T2R46) or Taste receptor type 2, member 38 (T2R38).

5. The method of claim 1, wherein the cell is a 16HBE cell or derivative thereof.

6. The method of claim 1, wherein the cell is modified to overexpress the bitter taste receptor.

7. The method of claim 1, wherein bitter taste receptor activity is measured by detecting the level of an intracellular second messenger in the cell.

8. The method of claim 7, wherein the second messenger is cAMP.

9. The method of claim 7, wherein the second messenger is DAG or IP3.

10. The method of claim 1, wherein bitter taste receptor activity is measured by detecting the level of intracellular calcium in the cell.

11. The method claim 1, wherein the bitter taste receptor activity is binding activity.

12. The method of claim 11, wherein a change in binding activity is detected by a competitive binding assay.

13. The method of claim 11, wherein a change in binding activity is detected by surface plasmon resonance.

14. A method for identifying a bitter tastant comprising: a) contacting a 16HBE cell or derivative thereof with a test compound; b) measuring bitter taste receptor activity, wherein an increase in bitter taste receptor activity indicates that the test compound is a bitter tastant.

15. The method of claim 14, wherein the bitter taste receptor is T2R46 or T2R38.

16. The method of claim 14, wherein bitter taste receptor activity is measured by detecting the level of an intracellular second messenger in the cell.

17. The method of claim 16, wherein the second messenger is cAMP.

18. The method of claim 16, wherein the second messenger is DAG or IP3.

19. The method of claim 14, wherein bitter taste receptor activity is measured by detecting the level of intracellular calcium in the cell.

20. The method of claim 14, wherein the bitter taste receptor activity is binding activity.

21. The method of claim 20, wherein binding activity is detected by a competitive binding assay.

22. The method of claim 20, wherein a change in binding activity is detected by surface plasmon resonance.

23. The method of claim 14, wherein the cell is modified to overexpress the bitter taste receptor.

* * * * *

```
                        SEQUENCE LISTING

<160> NUMBER OF SEQ ID NOS: 12

<210> SEQ ID NO 1
    <211> LENGTH: 6
    <212> TYPE: PRT
    <213> ORGANISM: Artificial sequence
    <220> FEATURE:
    <223> OTHER INFORMATION: Synthetic construct

<400> SEQUENCE: 1

Leu Pro Phe Asn Gln Leu
    1               5

<210> SEQ ID NO 2
    <211> LENGTH: 6
    <212> TYPE: PRT
    <213> ORGANISM: Artificial sequence
    <220> FEATURE:
    <223> OTHER INFORMATION: Synthetic construct

<400> SEQUENCE: 2

Leu Pro Phe Ser Gln Leu
    1               5

<210> SEQ ID NO 3
    <211> LENGTH: 17
    <212> TYPE: PRT
    <213> ORGANISM: Artificial sequence
    <220> FEATURE:
    <223> OTHER INFORMATION: Synthetic construct

<400> SEQUENCE: 3

Tyr Gln Glu Pro Val Leu Gly Pro Val Arg Gly Pro Phe Pro Ile Ile
    1               5                   10                  15

Val

<210> SEQ ID NO 4
    <211> LENGTH: 14
    <212> TYPE: PRT
    <213> ORGANISM: Artificial sequence
    <220> FEATURE:
    <223> OTHER INFORMATION: Synthetic construct

<400> SEQUENCE: 4

Pro Val Leu Gly Pro Val Arg Gly Pro Phe Pro Ile Ile Val
    1               5                   10

<210> SEQ ID NO 5
    <211> LENGTH: 10
```

```
<212> TYPE: PRT
<213> ORGANISM: Artificial sequence
<220> FEATURE:
<223> OTHER INFORMATION: Synthetic construct

<400> SEQUENCE: 5

Pro Val Arg Gly Pro Phe Pro Ile Ile Val
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic construct

<400> SEQUENCE: 6

Arg Gly Pro Phe Pro Ile Ile Val
1               5

<210> SEQ ID NO 7
<211> LENGTH: 1795
<212> TYPE: DNA
<213> ORGANISM: Homo sapiens

<400> SEQUENCE: 7
ggttaccact tggaaaacaa ttcatctgaa agaagcacag attttctcat ctatcctgtc      60
aacaaagaaa gaatcaagag agcaaggaca gtgatttccc ccgcattgca tttgtcttga    120
agatcagtca gaaagagaaa ctcggcatca tctgtgacag acagtggaac gaaaaatgcc    180
agtgaaatgc tgtttctaca ggtcaccaac tgcggaaaca atgacatggt ctgaaaatat    240
ggacacgctt ttagccaacc aagctggtct agatgctttt cgaatatttc taaaatcaga    300
gtttagtgaa gaaatgttg agttctggct tgcctgtgaa gactttaaga aaacgaaaaa     360
tgcagacaaa attgcttcca aagccaagat gatttattct gaattcattg aagctgatgc    420
acctaaagag attaacattg acttcggtac cagagacctc atctcaaaga atattgctga    480
accaacactc aaatgctttg atgaggctca gaaattaatc tattgtctca tggccaagga    540 ttcttttccct cgatttctga agtcagagat ttataaaaaa ctggtaaata gccaacaggt    600
tccaaatcat aaaaaatggc tcccttttt gtgaggaagg taaaagttaa ctaatcacta    660
tacttcaggg ctacaatatt ttaaatatac aagcatgatg cattgtcttt tgttttgttt    720
ttaggattta gaaacatttt tttacccaaa cagatgaata acgttttata caacaagcct    780
gaatttctaa ctcagttgtt tagaatgtat ttgcttacc agctatttaa tctcctactg    840
ggggagtaca agaaagttt atagagatac aatatagtct taaaccaaaa ctgaatattc    900
ttattatatt ataatgtaag gaattataca catcttcacg tggcagaatg aaagactttt    960
gagcatcata tacacaattt taaataccat tgctttattc aaaaaaatct cacttttgta  1020
aaaagagaat ttctgaacca aaatacaagt tttcatttaa tatatttaac tgttttttt   1080 ctgccatttc tttccaacta tttctaataa tgtggttatg aaaactgcta cgcctctcaa  1140
attatatttt ttaaatcaca ggaatgtata cacatttata tgtatgtctt gaatgcacca  1200
tggaccaaag tttttcaaaa tatatcactt ggctcaattc aatggcatca catataaaat  1260
gtgatgagtt atgtatgaaa aggcctcaag ggtggggaat actgatttc ttatgttaac   1320 agaaatataa aagaaagtgg aagactaagg agcatagata aatccttata agatgaagta  1380
tatagcaagt cataaaattt aagaatttgc aacattatct actcaattgt ggggaagtat  1440
```

| | | | | |
|---|---|---|---|---|
| ctattcactc | cttcagcact | gatacttgtt | tataaaaccc | aaacaatttt | taaatgcatt | 1500 |
| tattttgaga | tgttcctaaa | attgtttcat | tctatatgta | aatatcctgt | gataaatacg | 1560 |
| aataatttca | tttcaatatg | agaagctgta | aagattcaac | agatctccca | cgtttccatt | 1620 |
| ttctttgcac | agattatttt | atctgcattg | atatttctgc | ttttagattg | tttgaacatt | 1680 |
| aaaaaatgga | ggaaaaatag | catggcttat | tttatgtttt | cacaaactac | tcatttgata | 1740 |
| gacaaaattt | tgtcttccct | tcatcatgag | aaataaacat | ttaaacatat | tcaaa | 1795 |

<210> SEQ ID NO 8
<211> LENGTH: 152
<212> TYPE: PRT
<213> ORGANISM: Homo sapiens

<400> SEQUENCE: 8

```
Met Pro Val Lys Cys Cys Phe Tyr Arg Ser Pro Thr Ala Glu Thr Met
1               5                   10                  15

Thr Trp Ser Glu Asn Met Asp Thr Leu Leu Ala Asn Gln Ala Gly Leu
            20                  25                  30

Asp Ala Phe Arg Ile Phe Leu Lys Ser Glu Phe Ser Glu Glu Asn Val
        35                  40                  45

Glu Phe Trp Leu Ala Cys Glu Asp Phe Lys Lys Thr Lys Asn Ala Asp
    50                  55                  60

Lys Ile Ala Ser Lys Ala Lys Met Ile Tyr Ser Glu Phe Ile Glu Ala
65                  70                  75                  80

Asp Ala Pro Lys Glu Ile Asn Ile Asp Phe Gly Thr Arg Asp Leu Ile
                85                  90                  95

Ser Lys Asn Ile Ala Glu Pro Thr Leu Lys Cys Phe Asp Glu Ala Gln
            100                 105                 110

Lys Leu Ile Tyr Cys Leu Met Ala Lys Asp Ser Phe Pro Arg Phe Leu
        115                 120                 125

Lys Ser Glu Ile Tyr Lys Lys Leu Val Asn Ser Gln Gln Val Pro Asn
    130                 135                 140

His Lys Lys Trp Leu Pro Phe Leu
145                 150
```

<210> SEQ ID NO 9
<211> LENGTH: 930
<212> TYPE: DNA
<213> ORGANISM: Homo sapiens

<400> SEQUENCE: 9

| | | | | |
|---|---|---|---|---|
| atgataactt | ttctgcccat | catttttttcc | attctaatag | tggttacatt | tgtgattgga | 60 |
| aattttgcta | atggcttcat | agcattggta | aattccattg | agtggttcaa | gagacaaaag | 120 |
| atctcttttg | ctgaccaaat | tctcactgct | ctggcagtct | ccagagttgg | tttactctgg | 180 |
| gtattagtat | taaattggta | tgcaactgag | ttgaatccag | cttttaacag | tatagaagta | 240 |
| agaattactg | cttacaatgt | ctgggcagta | atcaaccatt | tcagcaactg | gcttgctact | 300 |
| agcctcagca | tatttatttt | gctcaagatt | gccaatttct | ccaaccttat | ttttcttcac | 360 |
| ttaaagagga | gagttaagag | tgttgttctg | gtgatactac | tggggccttt | gctattttttg | 420 |
| gtttgtcatc | tttttgtgat | aaacatgaat | cagattatat | ggacaaaaga | atatgaagga | 480 |
| aacatgactt | ggaagatcaa | actgaggagt | gcaatgtacc | tttcaaatac | aacggtaacc | 540 |
| atcctagcaa | acttagttcc | cttcactctg | accctgatat | cttttctgct | gttaatctgt | 600 |
| tctctgtgta | acatctcaa | aaagatgcag | ctccatggca | aaggatctca | agatcccagc | 660 |

```
atgaaggtcc acataaaagc tttgcaaact gtgacctcct tcctcttgtt atgtgccatt      720
tactttctgt ccataatcat gtcagtttgg agttttgaga gtctggaaaa caaacctgtc      780
ttcatgttct gcgaagctat tgcattcagc tatccttcaa cccacccatt catcctgatt      840
tggggaaaca agaagctaaa gcagactttt ctttcagttt tgtggcatgt gaggtactgg      900
gtgaaaggag agaagccttc atcttcatag                                       930
```

```
<210> SEQ ID NO 10
<211> LENGTH: 309
<212> TYPE: PRT
<213> ORGANISM: Homo sapiens

<400> SEQUENCE: 10
```

| | | | | | | | | | | | | | | |
|---|---|---|---|---|---|---|---|---|---|---|---|---|---|---|
| Met | Ile | Thr | Phe | Leu | Pro | Ile | Ile | Phe | Ser | Ile | Leu | Ile | Val | Val | Thr |
| 1 | | | | 5 | | | | | 10 | | | | | 15 | |
| Phe | Val | Ile | Gly | Asn | Phe | Ala | Asn | Gly | Phe | Ile | Ala | Leu | Val | Asn | Ser |
| | | | 20 | | | | | 25 | | | | | 30 | | |
| Ile | Glu | Trp | Phe | Lys | Arg | Gln | Lys | Ile | Ser | Phe | Ala | Asp | Gln | Ile | Leu |
| | | 35 | | | | | 40 | | | | | 45 | | | |
| Thr | Ala | Leu | Ala | Val | Ser | Arg | Val | Gly | Leu | Leu | Trp | Val | Leu | Val | Leu |
| 50 | | | | | 55 | | | | | 60 | | | | | |
| Asn | Trp | Tyr | Ala | Thr | Glu | Leu | Asn | Pro | Ala | Phe | Asn | Ser | Ile | Glu | Val |
| 65 | | | | | 70 | | | | | 75 | | | | | 80 |
| Arg | Ile | Thr | Ala | Tyr | Asn | Val | Trp | Ala | Val | Ile | Asn | His | Phe | Ser | Asn |
| | | | | 85 | | | | | 90 | | | | | 95 | |
| Trp | Leu | Ala | Thr | Ser | Leu | Ser | Ile | Phe | Tyr | Leu | Leu | Lys | Ile | Ala | Asn |
| | | | | 100 | | | | | 105 | | | | | 110 | |
| Phe | Ser | Asn | Leu | Ile | Phe | Leu | His | Leu | Lys | Arg | Arg | Val | Lys | Ser | Val |
| | | | 115 | | | | | 120 | | | | | 125 | | |
| Val | Leu | Val | Ile | Leu | Leu | Gly | Pro | Leu | Leu | Phe | Leu | Val | Cys | His | Leu |
| | 130 | | | | | 135 | | | | | 140 | | | | |
| Phe | Val | Ile | Asn | Met | Asn | Gln | Ile | Ile | Trp | Thr | Lys | Glu | Tyr | Glu | Gly |
| 145 | | | | | 150 | | | | | 155 | | | | | 160 |
| Asn | Met | Thr | Trp | Lys | Ile | Lys | Leu | Arg | Ser | Ala | Met | Tyr | Leu | Ser | Asn |
| | | | | 165 | | | | | 170 | | | | | 175 | |
| Thr | Thr | Val | Thr | Ile | Leu | Ala | Asn | Leu | Val | Pro | Phe | Thr | Leu | Thr | Leu |
| | | | 180 | | | | | 185 | | | | | 190 | | |
| Ile | Ser | Phe | Leu | Leu | Leu | Ile | Cys | Ser | Leu | Cys | Lys | His | Leu | Lys | Lys |
| | | 195 | | | | | 200 | | | | | 205 | | | |
| Met | Gln | Leu | His | Gly | Lys | Gly | Ser | Gln | Asp | Pro | Ser | Met | Lys | Val | His |
| | 210 | | | | | 215 | | | | | 220 | | | | |
| Ile | Lys | Ala | Leu | Gln | Thr | Val | Thr | Ser | Phe | Leu | Leu | Cys | Ala | Ile |
| 225 | | | | | 230 | | | | | 235 | | | | | 240 |
| Tyr | Phe | Leu | Ser | Ile | Ile | Met | Ser | Val | Trp | Ser | Phe | Glu | Ser | Leu | Glu |
| | | | | 245 | | | | | 250 | | | | | 255 | |
| Asn | Lys | Pro | Val | Phe | Met | Phe | Cys | Glu | Ala | Ile | Ala | Phe | Ser | Tyr | Pro |
| | | | 260 | | | | | 265 | | | | | 270 | | |
| Ser | Thr | His | Pro | Phe | Ile | Leu | Ile | Trp | Gly | Asn | Lys | Lys | Leu | Lys | Gln |
| | | 275 | | | | | 280 | | | | | 285 | | | |
| Thr | Phe | Leu | Ser | Val | Leu | Trp | His | Val | Arg | Tyr | Trp | Val | Lys | Gly | Glu |
| | 290 | | | | | 295 | | | | | 300 | | | | |
| Lys | Pro | Ser | Ser | Ser |
| 305 | | | | |

-continued

<210> SEQ ID NO 11
<211> LENGTH: 1143
<212> TYPE: DNA
<213> ORGANISM: Homo sapiens

<400> SEQUENCE: 11

| | | | | | |
|---|---|---|---|---|---|
| cctttctgca | ctgggtggca | accaggtctt | tagattagcc | aactagagaa | gagaagtaga | 60 |
| atagccaatt | agagaagtga | catcatgttg | actctaactc | gcatccgcac | tgtgtcctat | 120 |
| gaagtcagga | gtacatttct | gttcatttca | gtcctggagt | ttgcagtggg | gtttctgacc | 180 |
| aatgccttcg | ttttcttggt | gaattttttgg | gatgtagtga | agaggcaggc | actgagcaac | 240 |
| agtgattgtg | tgctgctgtg | tctcagcatc | agccggcttt | tcctgcatgg | actgctgttc | 300 |
| ctgagtgcta | tccagcttac | ccacttccag | aagttgagtg | aaccactgaa | ccacagctac | 360 |
| caagccatca | tcatgctatg | gatgattgca | aaccaagcca | acctctggct | tgctgcctgc | 420 |
| ctcagcctgc | tttactgctc | caagctcatc | cgtttctctc | acaccttcct | gatctgcttg | 480 |
| gcaagctggg | tctccaggaa | gatctcccag | atgctcctgg | gtattattct | ttgctcctgc | 540 |
| atctgcactg | tcctctgtgt | ttggtgcttt | tttagcagac | ctcacttcac | agtcacaact | 600 |
| gtgctattca | tgaataacaa | tacaaggctc | aactggcaga | ttaaagatct | caatttattt | 660 |
| tattcctttc | tcttctgcta | tctgtggtct | gtgcctcctt | tcctattgtt | tctggtttct | 720 |
| tctgggatgc | tgactgtctc | cctgggaagg | cacatgagga | caatgaaggt | ctataccaga | 780 |
| aactctcgtg | accccagcct | ggaggcccac | attaaagccc | tcaagtctct | tgtctccttt | 840 |
| ttctgcttct | ttgtgatatc | atcctgtgtt | gccttcatct | ctgtgcccct | actgattctg | 900 |
| tggcgcgaca | aaatagggt | gatggtttgt | gttgggataa | tggcagcttg | tccctctggg | 960 |
| catgcagcca | tcctgatctc | aggcaatgcc | aagttgagga | gagctgtgat | gaccattctg | 1020 |
| ctctgggctc | agagcagcct | gaaggtaaga | gccgaccaca | aggcagattc | ccggacactg | 1080 |
| tgctgagaat | ggacatgaaa | tgagctcttc | attaatacgc | ctgtgagtct | tcataaatat | 1140 |
| gcc | | | | | | 1143 |

<210> SEQ ID NO 12
<211> LENGTH: 333
<212> TYPE: PRT
<213> ORGANISM: Homo sapiens

<400> SEQUENCE: 12

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Lys Arg Gln
        35                  40                  45

Ala Leu Ser Asn Ser Asp Cys Val Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

-continued

```
Leu Ile Cys Leu Ala Ser Trp Val Ser Arg Lys Ile Ser Gln Met Leu
    130                 135                 140
Leu Gly Ile Ile Leu Cys Ser Cys Ile Cys Thr Val Leu Cys Val Trp
145                 150                 155                 160
Cys Phe Phe Ser Arg Pro His Phe Thr Val Thr Thr Val Leu Phe Met
                165                 170                 175
Asn Asn Asn Thr Arg Leu Asn Trp Gln Ile Lys Asp Leu Asn Leu Phe
            180                 185                 190
Tyr Ser Phe Leu Phe Cys Tyr Leu Trp Ser Val Pro Pro Phe Leu Leu
        195                 200                 205
Phe Leu Val Ser Ser Gly Met Leu Thr Val Ser Leu Gly Arg His Met
    210                 215                 220
Arg Thr Met Lys Val Tyr Thr Arg Asn Ser Arg Asp Pro Ser Leu Glu
225                 230                 235                 240
Ala His Ile Lys Ala Leu Lys Ser Leu Val Ser Phe Phe Cys Phe Phe
                245                 250                 255
Val Ile Ser Ser Cys Val Ala Phe Ile Ser Val Pro Leu Leu Ile Leu
            260                 265                 270
Trp Arg Asp Lys Ile Gly Val Met Val Cys Val Gly Ile Met Ala Ala
        275                 280                 285
Cys Pro Ser Gly His Ala Ala Ile Leu Ile Ser Gly Asn Ala Lys Leu
    290                 295                 300
Arg Arg Ala Val Met Thr Ile Leu Leu Trp Ala Gln Ser Ser Leu Lys
305                 310                 315                 320
Val Arg Ala Asp His Lys Ala Asp Ser Arg Thr Leu Cys
                325                 330
```